United States Patent [19]

Midou et al.

[11] Patent Number: 5,723,407
[45] Date of Patent: Mar. 3, 1998

[54] SULFONYLSEMICARBAZIDE DERIVATIVES AND PRESERVATIVE COMPOSITION FOR PRESERVING THE FRESHNESS OF FLOWER OF CUT FLOWERS

[75] Inventors: Naoki Midou; Kuniomi Matsumoto; Michiaki Iwata, all of Kanagawa-ken; Kunihiko Kurihara; Kunitaka Tachibana, both of Tokyo, all of Japan

[73] Assignee: Meiji Seika Kaisha, Ltd., Tokyo, Japan

[21] Appl. No.: 596,292

[22] PCT Filed: Aug. 16, 1994

[86] PCT No.: PCT/JP94/01358

§ 371 Date: Feb. 13, 1996

§ 102(e) Date: Feb. 13, 1996

[87] PCT Pub. No.: WO95/05362

PCT Pub. Date: Feb. 23, 1995

[30] Foreign Application Priority Data

Aug. 16, 1993 [JP] Japan ............ 5-202380

[51] Int. Cl.$^6$ ............ A01N 3/02; C07D 213/16; C07D 333/10
[52] U.S. Cl. ............ 504/115; 504/114; 546/293; 549/2; 549/65
[58] Field of Search ............ 564/35; 514/590, 514/529, 532, 347, 445; 560/13; 546/293; 549/64.2, 65; 544/164; 504/114, 115

[56] References Cited

FOREIGN PATENT DOCUMENTS

| | | |
|---|---|---|
| 1668339 | 1/1972 | Germany. |
| 39-12638 | 7/1938 | Japan. |
| 39-12639 | 7/1939 | Japan. |
| 39-12640 | 7/1939 | Japan. |
| 40-2424 | 2/1940 | Japan. |
| 40-2425 | 2/1940 | Japan. |
| 57-206651 | 12/1982 | Japan. |
| 282558 | 12/1964 | Netherlands. |

*Primary Examiner*—Shailendra Kumar
*Attorney, Agent, or Firm*—Birch, Stewart, Kolasch & Birch, LLP

[57] ABSTRACT

A sulfonylsemicarbazide derivative of the general formula (I) is effective as a preservative agent for preserving the freshness of a flower, which can prolong the vase life of the flower petals of cut flowers where the flowers can be enjoyed.

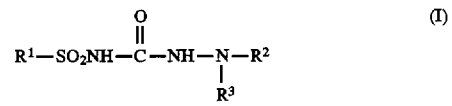

wherein $R^1$ represents a $(C_3-C_4)$-alkyl group, a substituted or unsubstituted phenyl group, a pyridyl group, a thiophenyl group or others, $R^2$ and $R^3$ each independently represent a hydrogen atom, a lower alkyl group, an alkoxalyl group, an alkoxyalkyl group, a group of the formula —C(X)—X—$R^4$ where X means an oxygen atom or a sulfur atom and $R^4$ means an alkyl group, or other, or $R^2$ and $R^3$ may form a heterocyclic ring having 4 to 5 carbon atoms or a group of the formula —N=$CR^5(R^6)$, as taken with the —N atom to which $R^2$ and $R^3$ are attached.

11 Claims, No Drawings

5,723,407

SULFONYLSEMICARBAZIDE DERIVATIVES AND PRESERVATIVE COMPOSITION FOR PRESERVING THE FRESHNESS OF FLOWER OF CUT FLOWERS

This application is a 371 of PCT/US94/01358 filed Aug. 16, 1994.

TECHNICAL FIELD

This invention relates to a preservative composition or agent for preserving the freshness of flower petals of cut flowers, which contains a known or novel sulfonylsemicarbazide derivative as the effective ingredient. Further, the present invention also relates to the novel sulfonylsemicarbazide derivatives which have such activities that can preserve the freshness of flower petals of the cut flowers and can extend or prolong the vase life of the cut flowers where the flower petals thereof can be worthy of being appreciated. In addition, the present invention pertains to a method for preserving the freshness of flower petals of a plant capable of blooming ornamental flowers, in other words, the flower petals of a plant of the florist crop, which method comprises treatment with said sulfonylsemicarbazide derivatives.

Described specifically, the sulfonylsemicarbazide derivatives which are useful according to the present invention in the treatment for preserving the freshness of the flower petals are such sulfonylsemicarbazide derivatives having the following general formula (I):

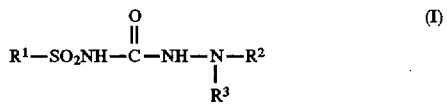

wherein $R^1$ represents a linear or branched, lower alkyl group having 3 to 4 carbon atoms, or a phenyl group which may optionally be substituted by one or more halogen atoms, lower alkyl groups, hydroxyl groups, alkoxyl groups, carboxyl groups, alkoxycarbonyl groups, nitro groups, amino groups or benzyloxy groups, or $R^1$ represents a pyridyl group, or a thiophenyl group which may optionally be substituted by one or more carboxyl groups or alkoxycarbonyl groups, and $R^2$ and $R^3$ each independently represents a hydrogen atom, a lower alkyl group, an alkoxalyl group, an alkoxyalkyl group, an alkoxycarbonyl group or an alkylthio-thiocarbonyl group represented by the formula —C(X)—X—$R^4$ where X means an oxygen atom or a sulfur atom and $R^4$ means a lower alkyl group, or $R^2$ and $R^3$ may form a heterocyclic ring having 4 to 5 carbon atoms, as taken with the nitrogen atom to which $R^2$ and $R^3$ are bonded, or $R^2$ and $R^3$ may form a group of the formula —N=$CR^5(R^6)$ where $R^5$ and $R^6$ mean lower alkyl groups, respectively, as taken with the nitrogen atom to which $R^2$ and $R^3$ are bonded, or salts of said derivatives.

BACKGROUND ART

Causes for which the freshness of flower petals of the cut flowers can be reduced or lost, include, for example, such bacterial decay or rotting and blockage of the vessels occurring in the stem portions of the cut flowers in the vase water where the cut flowers are soaked, as well as, full exhaustion of nutrients, and an increased concentration of ethylene, an aging hormone, inside the plant bodies of the cut flowers, or others. To prevent the bacterial decay and blockage of the vessels in the stems of cut flowers, it has been proposed to add a bactericide, such as 8-hydroxyquinoline, or aluminum sulfate to the vase water.

The addition of aluminum sulfate is made to cause settling of the particles of dirts as formed in the vase water. It has also been proposed to add various surfactants to the vase water in order to enhance the water uptake by the cut flowers. To avoid full exhaustion of nutrients in cut flowers, it is known that a saccharide such as sugar is added to the vase water. The effects of these additives can however be varying and are not always attainable to a noticeable extent.

On the other hand, in order to prevent an increase in the concentration of ethylene which is an aging hormone of plants, there is proposed the method which was discovered by Veen et al. in 1978 in the Netherlands and involves a treatment with silver thiosulfate (abbreviated as "STS") ("Planta", 140, pp. 93–96 (1978)). STS is known to inhibit the action of ethylene and hence to clearly exhibit its effects that can preserve or retain the freshness of flower petals for a prolonged period for such cut flowers of carnation, perennial baby's breadth or the like, where wilting of the flower petals is primarilly attributable to ethylene.

Nowadays, growers of the cut flowers are using STS as the preservative agent for the freshness of various cut flowers. However, STS involves a potential problem of environmental pollution due to that STS contains silver, a heavy metal, as its active component. Presently, there is a strong desire for a heavy metal-free and safe preservative agent for preserving or retaining the freshness of cut flowers. As a matter of fact, use of STS has already been restricted legally in the Netherlands, and as a substitute for STS, there is employed in practice amino-oxyacetic acid which inhibits biosynthesis of ethylene ("Hortscience"15, pp. 805–806 (1980)). This compound is however diadvantageous in that it is expensive, is applicable to limited kinds of flowers and is less effective than STS.

Further, L-α-(2-aminoethoxyvinyl)glycine and 2-aminoisobutyric acid are also known to exhibit their effects of preserving the freshness of flower petals of cut flowers by their inhibiting the biosynthesis of ethylene ("Journal of The American Society for Horticultural Science"102, pp. 517–520 (1977); and "Scientia Horticulturae"44, pp. 127–134 (1990)). It is known also that combined use of the above-described two compounds can enhance the effects of retaining the freshness of flower petals of cut flowers (Japanese Patent Application "Kokai" No. 238901/93). However, these compounds are not practically used because their prices are high compared with their attainable effects.

Several sulfonylsemicarbazide derivatives, along with their preparation processes, are known to be useful as antidiabetics ("Acta Chemica Scandinavica"20, pp. 2795–2806 (1966) and "Chemical and Pharmaceutical Bulletin"26, pp. 472–480 (1978)) and also useful as agricultural and horticultural fungicides (Japanese Patent Application "Kokai" No. 206651/82). However, these known sulfonylsemicarbazide derivatives were not known at all in the past to have the effects to preserve the freshness of flowers of cut flowers.

DISCLOSURE OF THE INVENTION

An object of the present invention is to provide such a novel preservative agent for preserving the freshness of flower petals of cut flowers, which has excellent effects for preserving or retaining the freshness of cut flowers for a prolonged period so that the vase life of the cut flowers worthy of being enjoyed can be extended.

With a view to achieving the above object, the present inventors have synthesized a number of compounds and conducted an extensive investigation on the physiological action of these compounds upon cut flowers. As a result, the present inventors have found that a number of known or novel sulfonylsemicarbazide derivatives collectively represented by the following general formula (I):

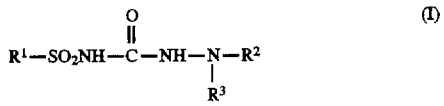

wherein $R^1$ represents a linear or branched, lower alkyl group having 3 to 4 carbon atoms, or a phenyl group which may optionally be substituted by one or more halogen atoms, lower alkyl groups, hydroxyl groups, alkoxyl groups, carboxyl groups, alkoxycarbonyl groups, nitro groups, amino groups or benzyloxy groups, or $R^1$ represents a pyridyl group, or a thiophenyl group which may optionally be substituted by one or more carboxyl groups or alkoxycarbonyl groups, and $R^2$ and $R^3$ each independently represents a hydrogen atom, a lower alkyl group, an alkoxalyl group, an alkoxyalkyl group, an alkoxycarbonyl group or an alkylthio-thiocarbonyl group represented by the formula —C(X)—X—$R^4$ where X means an oxygen atom or a sulfur atom and $R^4$ means a lower alkyl group, or $R^2$ and $R^3$ may form a heterocyclic ring having 4 to 5 carbon atoms, as taken with the nitrogen atom to which $R^2$ and $R^3$ are bonded, or $R^2$ and $R^3$ may form a group of the formula —N=$CR^5(R^6)$ where $R^5$ and $R^6$ mean lower alkyl groups, respectively, as taken with the nitrogen atom to which $R^2$ and $R^3$ are bonded, or salts of said derivatives, have not only such effects for preserving the freshness of flower petals of cut flowers, but also such effects for retaining for a prolonged period the freshness of flowers of plants of the florist crop which are growing in soil or other cultivating media under cultivation for the production of cut flowers. And thus the present inventors have achieved the present invention.

According to a first aspect of the present invention, therefore, there is provided a composition for preserving the freshness of flower of cut flowers, characterized in that said composition comprises as an effective ingredient at least one of such sulfonylsemicarbazide derivatives having the general formula (I):

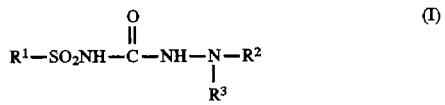

wherein $R^1$ represents a linear or branched, lower alkyl group having 3 to 4 carbon atoms, or a phenyl group which may optionally be substituted by one or more halogen atoms, lower alkyl groups, hydroxyl groups, alkoxyl groups, carboxyl groups, alkoxycarbonyl groups, nitro groups, amino groups or benzyloxy groups, or $R^1$ represents a pyridyl group, or a thiophenyl group which may optionally be substituted by one or more carboxyl groups or alkoxycarbonyl groups, and $R^2$ and $R^3$ each independently represents a hydrogen atom, a lower alkyl group, an alkoxalyl group, an alkoxyalkyl group, an alkoxycarbonyl group or an alkylthio-thiocarbonyl group represented by the formula —C(X)—X—$R^4$ where X means an oxygen atom or a sulfur atom and $R^4$ means a lower alkyl group, or $R^2$ and $R^3$ may form a heterocyclic ring having 4 to 5 carbon atoms, as taken with the nitrogen atom to which $R^2$ and $R^3$ are bonded, or $R^2$ and $R^3$ may form a group of the formula —N=$CR^5(R^6)$ where $R^5$ and $R^6$ mean lower alkyl groups, respectively, as taken with the nitrogen atom to which $R^2$ and $R^3$ are bonded, or salts of said derivatives, and also comprises a liquid or solid carrier for the effective ingredient.

With respect to the above-described general formula (I), the term "lower alkyl group" means an alkyl group having 1 to 6 carbon atoms, with an alkyl group having 1 to 4 carbon atoms being preferred. The alkoxyl group is preferably an alkoxyl group having 1 to 6 carbon atoms. The alkoxycarbonyl group is preferably an alkoxy-carbonyl group having 2 to 7 carbon atoms.

The preferred alkoxyalkyl group is a ($C_1$–$C_4$)-alkoxy-($C_1$–$C_4$)alkyl group. The preferred alkylthio group is a ($C_1$–$C_4$)alkylthio group.

The term "the salts of the sulfonylsemicarbazide derivatives of the general formula (I)" embraces the sodium salt, the potassium salt, the ammonium salt, the polyethanolamine addition salt, the isopropylamine addition salt, and addition salts with tri-lower alkyl amines such as trimethylamine.

BEST MODE FOR CARRYING OUT THE INVENTION

Specific examples of the sulfonylsemicarbazide derivatives of the general formula (I) are shown in Table 1 and Table 2 given hereinafter. It is however to be noted that compounds usable in the present invention are not limited only to the compounds shown in Table 1 and Table 2. Incidentally, the Compound Nos. in the tables will be referred to Synthesis Examples and Tests as described hereinafter.

TABLE 1

Formula (I)

$R^1-SO_2-NH-C(=O)-NH-N(R^3)-R^2$

| Compound No. | $R^1$ | $R^2$ | $R^3$ |
|---|---|---|---|
| 1 | $H_3C$—C$_6$H$_4$— | $CH_3$ | H |
| 2 | C$_6$H$_5$— | $CH_3$ | H |

TABLE 1-continued

Formula (I)

$$R^1-SO_2-NH-\overset{\overset{O}{\|}}{C}-NH-\underset{\underset{R^3}{|}}{N}-R^2$$

| Compound No. | R¹ | R² | R³ |
|---|---|---|---|
| 3 | phenyl | CH₃ | CH₃ |
| 4 | phenyl | C₂H₅ | C₂H₅ |
| 5 | 4-H₃C-phenyl | CH₃ | CH₃ |
| 6 | 2-CH₃-phenyl | CH₃ | CH₃ |
| 7 | 4-F-phenyl | CH₃ | CH₃ |
| 8 | 4-Cl-phenyl | CH₃ | CH₃ |
| 9 | 4-Br-phenyl | CH₃ | CH₃ |
| 10 | 4-HO-phenyl | CH₃ | CH₃ |
| 11 | 4-H₃CO-phenyl | CH₃ | CH₃ |
| 12 | 4-H₃COOC-phenyl | CH₃ | CH₃ |
| 13 | 4-O₂N-phenyl | CH₃ | CH₃ |
| 14 | 4-H₂N-phenyl | CH₃ | CH₃ |
| 15 | phenyl | C₂H₄OC₂H₅ | C₂H₄OC₂H₅ |

TABLE 1-continued

Formula (I)

$$R^1-SO_2-NH-\overset{O}{\underset{\|}{C}}-NH-\underset{\underset{R^3}{|}}{N}-R^2$$

| Compound No. | $R^1$ | $R^2$ | $R^3$ |
|---|---|---|---|
| 16 | 4-H₃C-C₆H₄- | C₂H₄OC₂H₅ | C₂H₄OC₂H₅ |
| 17 | 4-Cl-C₆H₄- | C₂H₄OC₂H₅ | C₂H₄OC₂H₅ |
| 18 | C₆H₅- | H | COOCH₃ |
| 19 | C₆H₅- | H | COOC₂H₅ |
| 20 | 4-H₃C-C₆H₄- | H | COOC₂H₅ |
| 21 | C₆H₅- | H | CSSC₂H₅ |
| 22 | 4-H₃C-C₆H₄- | H | CSSCH₃ |
| 23 | C₆H₅- | CH₃ | COCOOCH₃ |
| 24 | 4-(C₆H₅CH₂O)-C₆H₄- | CH₃ | CH₃ |
| 25 | H₃C-CH₂-CH₂- | CH₃ | CH₃ |
| 26 | (CH₃)₂CH- | CH₃ | CH₃ |
| 27 | 2-pyridyl | CH₃ | CH₃ |
| 28 | 3-pyridyl | CH₃ | CH₃ |
| 29 | 2-thienyl | CH₃ | CH₃ |

TABLE 1-continued $$R^1-SO_2-NH-\overset{\overset{O}{\|}}{C}-NH-\underset{\underset{R^3}{|}}{N}-R^2 \quad \text{Formula (I)}$$

| Compound No. | $R^1$ | $R^2$ | $R^3$ |
|---|---|---|---|
| 30 | HOOC—⟨thiophene⟩— | $CH_3$ | $CH_3$ |
| 31 | $H_3COOC$—⟨thiophene⟩— | $CH_3$ | $CH_3$ |

TABLE 2

$$R^1-SO_2-NH-\overset{\overset{O}{\|}}{C}-NH-A \quad \text{Formula (I')}$$

| Compound No. | $R^1$ | A |
|---|---|---|
| 32 | $H_3C$—⟨phenyl⟩— | —N⟨morpholine⟩O |
| 33 | ⟨phenyl⟩— | —N⟨morpholine⟩O |
| 34 | Cl—⟨phenyl⟩— | —N⟨morpholine⟩O |
| 35 | $H_3C$—⟨phenyl⟩— | —N⟨piperidine⟩ |
| 36 | ⟨phenyl⟩— | —N⟨piperidine⟩ |
| 37 | $H_3C$—⟨phenyl⟩— | —N=C(CH_3)(CH_3) |

The compounds of Compound No. 3, No. 4, No. 8, No. 9, No. 11, No. 13 and No. 14 shown in Table 1, and the compounds of Compound No. 34 and No. 36 presented in Table 2 are known compounds disclosed in the Chemical Abstracts Registry File. The compound of Compound No. 5 shown in Table 1 is a known compound disclosed in "Acta Chemica Scandinavica" 20, pp. 2795–2806 (1966) referred to above, while the compounds of Compounds No. 32 and No. 35 shown in Table 2 are known compounds disclosed in "J. Med. Pharm. Chem."5, pp. 815–822 (1962).

The remaining compounds shown in Table 1 and Table 2 are all novel compounds which have not been disclosed in any publication. However, Compound No. 12 shown in Table 1 is embraced in the phenylsulfonylsemicarbazide derivative represented by the general formula shown in claim 1 of the above-mentioned Japanese Patent Application "Kokai" No. 206651/82, although it is not specifically described in the specification of said application as published.

With respect to some of the novel compounds shown in Table 1 and Table 2, their melting points as the physical properties of the compounds are presented in Table 3 and Table 4 given hereinafter.

Preferred examples of the compound which are employed as the effective ingredient in the composition for preserving the freshness of flowers according to the first aspect of the present invention include such sulfonylsemicarbazide derivatives having the following general formulae (I-a), (I-b), (I-c), (I-d), (I-e), (I-f), (I-h) and (I-i), and salts thereof.

(1) Sulfonylsemicarbazide derivatives represented by the following general formula (I-a):

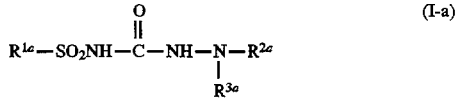

$$R^{1a}-SO_2NH-\overset{\overset{O}{\|}}{C}-NH-\underset{\underset{R^{3a}}{|}}{N}-R^{2a} \quad \text{(I-a)}$$

wherein $R^{1a}$ is a linear or branched, lower alkyl group having 3 to 4 carbon atoms, a phenyl group, a 2-tolyl group, a fluorophenyl group, a hydroxyphenyl group, a benzyloxyphenyl group, an alkoxycarbonylphenyl group or a pyridyl group, or $R^{1a}$ is a thiophenyl group which may optionally be substituted by one or more carboxyl groups or alkoxycarbonyl groups, and $R^{2a}$ and $R^{3a}$ are lower alkyl groups, respectively.

(2) Sulfonylsemicarbazide derivatives represented by the following general formula (I-b):

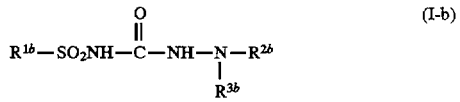

$$R^{1b}-SO_2NH-\overset{\overset{O}{\|}}{C}-NH-\underset{\underset{R^{3b}}{|}}{N}-R^{2b} \quad \text{(I-b)}$$

wherein $R^{1b}$ is a phenyl group which may be substituted by one or more lower alkyl groups, and one of $R^{2b}$ and $R^{3b}$ is a hydrogen atom but the other one of $R^{2b}$ and $R^{3b}$ is a lower alkyl group, preferably methyl group.

(3) Sulfonylsemicarbazide derivatives represented by the following general formula (I-c):

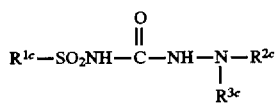

(I-c)

wherein $R^{1c}$ is a phenyl group which may be substituted by one or more lower alkyl groups or halogen atoms, and $R^{2c}$ and $R^{3c}$ are lower alkoxyalkyl groups, respectively.

(4) Sulfonylsemicarbazide derivatives represented by the following general formula (I-d):

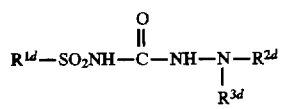

(I-d)

wherein $R^{1d}$ is a phenyl group which may be substituted by one or more lower alkyl groups, and one of $R^{2d}$ and $R^{3d}$ is an alkoxalyl group or an alkoxycarbonyl group or alkylthiothiocarbonyl group represented by the formula —C(X)—X—$R^4$ where X means an oxygen atom or a sulfur atom and $R^4$ means a lower alkyl group, but the other one of $R^{2d}$ and $R^{3d}$ is a hydrogen atom or a lower alkyl group.

(5) Sulfonylsemicarbazide derivatives represented by the following general formula (I-e):

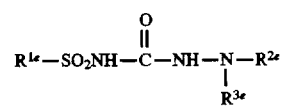

(I-e)

wherein $R^{1e}$ is a phenyl group which may be substituted by one or more lower alkyl groups or halogen atoms, and $R^{2e}$ and $R^{3e}$ form a morpholino group or a piperidino group, as taken with the nitrogen atom to which $R^{2e}$ and $R^{3e}$ are bonded.

(6) Sulfonylsemicarbazide derivatives represented by the following general formula (I-f):

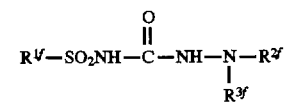

(I-f)

wherein $R^{1f}$ is a phenyl group which may be substituted by one or more lower alkyl groups, and $R^{2f}$ and $R^{3f}$ form a group of the formula —N=$CR^5(R^6)$ where $R^5$ and $R^6$ each independently mean a lower alkyl group, as taken with the nitrogen atom to which $R^{2f}$ and $R^{3f}$ are bonded.

(7) Sulfonylsemicarbazide derivatives represented by the following general formula (I-g):

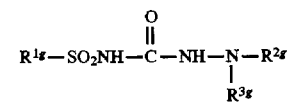

(I-g)

wherein $R^{1g}$ is a linear or branched, lower alkyl group having 3 to 4 carbon atoms, and $R^2g$ and $R^3g$ are alkyl groups having 1 to 2 carbon atoms, respectively.

(8) Sulfonylsemicarbazide derivatives represented by the following general formula (I-h):

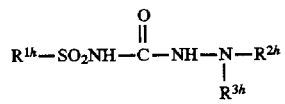

(I-h)

wherein $R^{1h}$ is a pyridine-2-yl group or a pyridine-3-yl group, and $R^{2h}$ and $R^{3h}$ are alkyl groups having 1 to 2 carbon atoms, respectively.

(9) Sulfonylsemicarbazide derivatives represented by the following general formula (I-i):

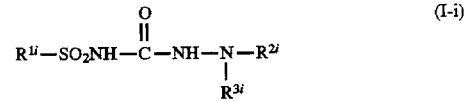

(I-i)

wherein $R^{1i}$ is a thiophen-2-yl or thiophen-3-yl group which may be substituted by one or more carboxyl groups or lower alkoxycarbonyl groups, and $R^{2i}$ and $R^{3i}$ are alkyl groups having 1 to 2 carbon atoms, respectively Particularly preferred examples of the compound of the general formula (I) which may be employed as the effective ingredient in the composition according to the first aspect of the present invention include the following compounds (i) to (vii):

(i) 1,1-Dimethyl-4-(phenylsulfonyl)semicarbazide (Compound No. 3 in Table 1)

(ii) 1,1-Dimethyl-4-(p-methylphenylsulfonyl)-semicarbazide (Compound No. 5 in Table 1)

(iii) 1,1-Dimethyl-4-(p-chlorophenylsulfonyl)-semicarbazide (Compound No. 8 in Table 1)

(iv) 1,1-Dimethyl-4-(p-nitrophenylsulfonyl)-semicarbazide (Compound No. 13 in Table 1)

(v) 1,1-Dimethyl-4-(pyridine-2-ylsulfonyl)-semicarbazide (Compound No. 27 in Table 1)

(vi) 1,1-Dimethyl-4-(thiophen-2-ylsulfonyl)-semicarbazide (Compound No. 29 in Table 1)

(vii) 1-(2-Propanone)-4-(p-methylphenylsulfonyl)-semicarbazone (Compound No. 37 in Table 2)

In the composition for preserving flowers according to the first aspect of the present invention, the effective ingredient compound of the general formula (I) is incorporated in the composition in admixture with a liquid carrier which may be a solvent, for example, water, an alcohol such as methanol or ethanol, a ketone such as acetone, pentanone, cyclohexanone or isophorone, an ester such as ethyl acetate, butyl acetate or diethyl sebacate, an ether such as methyl cellosolve or ethyl cellosolve, an aromatic hydrocarbon such as benzene or xylene, an aliphatic hydrocarbon such as kerosine or liquid paraffin, dimethylformamide, or dimethylsulfoxide or a mixed solvent of two or more of them, so that the effective ingredient is dissolved in such solvent. Adjuvants such as surfactants, inorganic or organic amines or acids, saccharides and gums may be incorporated therein further, as needed.

Further, the composition according to the first aspect of the present invention can also be formulated by mixing and diluting the compound of the general formula (I) appropriately with a solid carrier, for example, clay minerals, starch, a saccharide, a salt such as sodium bicarbonate or mirabilite, or an organic acid. Besides, the composition can also be formulated into aqueous solution, oil-base solution, suspension, emulsion, cream, paste, and various solid preparations such as powder, granules and tablets with using such additives as described above. Upon use, the composition may be diluted in water or the like as needed, before it is applied to plants.

When the various preparations of the composition according to the present invention are produced, it is necessary that the content of the compound of the general formula (I) in the preparation is changed appropriately in accordance with the purpose and manner of their application, because these preparations can be applied in a wide range of situations. When the preparation is applied directly to a plant, it is necessary to ensure that this preparation contains the compound of the general formula (I) at such a concentration at which the compound is practically applied. To formulate a highly concentrated preparation, it is desired to incorporate the compound of the general formula (I) in a proportion of 5 to 80%, preferably 10 to 40% by weight in the preparation.

In the composition for preserving the freshness of flowers according to the first aspect of the present invention, additives such as bactericides and other agents, other commercially available agents for preserving the freshness of flowers, nutrient replenishers and others can be incorporated additionally, as desired.

The sulfonylsemicarbazide derivative having the general formula (I) or the salt thereof can be applied in the form of a composition which is prepared by mixing it with a carrier as described above. However, the compound of the general formula.(I) may also be used as such for the effective ingredient, that is to say, as an agent for preserving the freshness of flower petals of cut flowers, without said compound being mixed with a carrier.

In a second aspect of the present invention, there is accordingly provided an agent for preserving the freshness of flowers of cut flowers, which comprises the sulfonylsemicarbazide derivative of the general formula (I) or the salt thereof as an effective ingredient.

The composition for preserving the freshness of flower petals of cut flowers according to the first aspect of the present invention, as well as the agent for preserving the freshness of flowers according to the second aspect of the present invention can be both applied to plants of cut flowers by spraying, soaking, drenching and so on. A variety of known application methods can be adopted in view of the properties of the compound of the general formula (I). In general, it is possible to adopt such a method in which the whole body of a plant is entirely sprayed with a solution, dispersion or suspension containing the compound the general formula (I), or such a method in which either a root portion of a plant of the florist crop for producing the cut flowers or a cut stem portion of the cut flowers after its harvesting is soaked in a treating solution containing the compound of the general formula (I), so that said compound is absorbed in the plant body. According to one method for the treatment, it is only necessary to soak the cut stem portions of the cut flowers for at least 1 hour, preferably 1 to 24 hours in the treating solution containing the compound of the general formula (I). According to another treatment method, cut flowers can be placed and stored in a flower vase which is filled with water containing the compound of the general formula (I) added therein.

No particular limitation is imposed on the concentration used of the compound of the general formula (I) because optimal value of the concentration can vary depending on the kind and state of a flower to which said compound is to be applied. Preferably, the compound of the general formula (I) may be used at a concentration in a range of from $1 \times 10^{-4}$ to 0.1 wt. % by dissolving or dispersing in water.

Illustrative examples of flowers, for which the composition or agent for preserving the freshness of flowers according to the present invention is effective, include carnation, delphinium, sweet pea, perennial baby's breath, lily, freesia, tulip and orchid. The present invention can be applied to plants of the florist crop under cultivation in fields, plants of the florist crop after transplantion to planters or pots and cut flowers as harvested by cutting off their root parts either at intermediate portions or at lower end portions of the stems of plants of the florist crop.

In a third aspect of the present invention, there is thus provided a method for preserving the freshness of flower of a plant of the florist crop, which comprises treating the cut stem portion or leaves of the cut flowers as obtained by cutting off the root part of the florist plant, or treating roots or leaves of the florist plant under cultivation in a field or a pot, with such a sulfonylsemicarbazide derivative having the general formula (I):

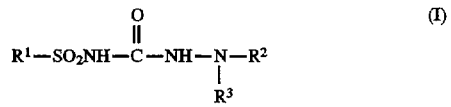

wherein $R^1$ represents a linear or branched, lower alkyl group having 3 to 4 carbon atoms, or a phenyl group which may optionally be substituted by one or more halogen atoms, lower alkyl groups, hydroxyl groups, alkoxyl groups, carboxyl groups, alkoxycarbonyl groups, nitro groups, amino groups or benzyloxy groups, or $R^1$ represents a pyridyl group, or a thiophenyl group which may optionally be substituted by one or more carboxyl groups or alkoxycarbonyl groups, and $R^2$ and $R^3$ each independently represents a hydrogen atom, a lower alkyl group, an alkoxalyl group, an alkoxyalkyl group, an alkoxycarbonyl group or an alkylthio-thiocarbonyl group represented by the formula —C(X)—X—$R^4$ where X means an oxygen atom or a sulfur atom and $R^4$ means a lower alkyl group, or $R^2$ and $R^3$ may form a heterocyclic ring having 4 to 5 carbon atoms, as taken with the nitrogen atom to which $R^2$ and $R^3$ are bonded, or $R^2$ and $R^3$ may form a group of the formula —N=CR$^5$(R6) where $R^5$ and $R^6$ mean lower alkyl groups, respectively, as taken with the nitrogen atom to which $R^2$ and $R^3$ are bonded, or salts of said derivatives, or with an aqueous solution of said derivative(s) or said salt(s), and thereby allowing the cut flowers or the florist plant under the cultivation to absorb the compound of the general formula (I) in an amount effective to maintain the freshness of the flower.

When the cut stem portion of cut flower is treated in accordance with the method of the third aspect of the present invention, the treatment can be conducted by soaking the cut stem portion of the plant for at least 1 hour, for example, 1 to 24 hours in an aqueous solution containing said compound at a concentration in a range of from $1 \times 10^{-4}$ wt. % to 0.1 wt. %, so as to make the effective compound adsorbed by the cut flower. On the other hand, when a plant of the florist crop under cultivation is treated, it is possible to adopt a method in which the treatment is conducted by spraying the cultivating soil or other medium with an aqueous solution containing the compound of the general formula (I) at an increased concentration higher than the above-described concentration range so that said compound can penetrate into the cultivation medium. The increased concentration of the active compound in the spraying solution should be needed to allow for losses of the active compound due to the adsorption of the compound by the cultivation soil and the flowing-away of the spraying solution.

In a fourth aspect of the present invention, there is also provided a use of a sulfonylsemicarbazide derivative or a salt thereof in the manufacture of a preservative agent for the freshness of a flower, said sulfonylsemi-carbazide derivative having the general formula (I):

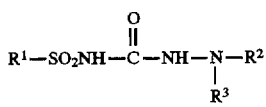 (I)

wherein $R^1$ represents a linear or branched, lower alkyl group having 3 to 4 carbon atoms, or a phenyl group which may optionally be substituted by one or more halogen atoms, lower alkyl groups, hydroxyl groups, alkoxyl groups, carboxyl groups, alkoxycarbonyl groups, nitro groups, amino groups or benzyloxy groups, or $R^1$ represents a pyridyl group, or a thiophenyl group which may optionally be substituted by one or more carboxyl groups or alkoxycarbonyl groups, and $R^2$ and $R^3$ each independently represents a hydrogen atom, a lower alkyl group, an alkoxalyl group, an alkoxyalkyl group, an alkoxycarbonyl group or an alkylthio-thiocarbonyl group represented by the formula —C(X)—X—$R^4$ where X means an oxygen atom or a sulfur atom and $R^4$ means a lower alkyl group, or $R^2$ and $R^3$ may form a heterocyclic ring having 4 to 5 carbon atoms, as taken with the nitrogen atom to which $R^2$ and $R^3$ are bonded, or $R^2$ and $R^3$ may form a group of the formula —N=CR$^5$(R$^6$) where $R^5$ and $R^6$ mean lower alkyl groups, respectively, as taken with the nitrogen atom to which $R^2$ and $R^3$ are bonded.

The sulfonylsemicarbazide derivative of the general formula (I) which is concerned with the present invention can be readily prepared in accordance with reaction equations shown below, as Process A or Process B.

Process A

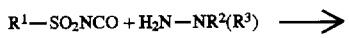
(II)        (III)

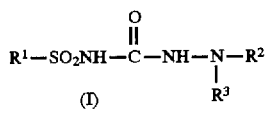
(I)

Process B

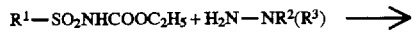
(IV)        (III)

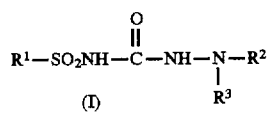
(I)

In the reaction equations, $R^1$, $R^2$ and $R^3$ have the same meanings as defined above in the general formula (I) shown hereinbefore.

In Process A, the sulfonyl isocyanate (II) is dissolved in an anhydrous solvent such as methylene chloride, benzene, toluene, tetrahydrofuran or dioxane, followed by the addition of the hydrazine (III) with stirring under ice cooling or at room temperature, so that the reaction proceeds promptly to give the target sulfonylsemicarbazide derivative (I) readily.

In Process B, on the other hand, the sulfonyl carbamate (IV) and the hydrazine (III) are reacted with each other at 105° to 120° C. by mixing them together or dissolving them in a solvent such as toluene or xylen, whereby the target sulfonylsemicarbazide derivative (I) can be produced in a high yield.

Some of the compounds of the general formula (I) which are useful as the effective ingredients in the composition according to the first aspect of the present invention or the agent according to the second aspect of the present invention are known compounds, but the remaining compounds are novel compounds which are not disclosed in any publications.

In a fifth aspect of the present invention, there is accordingly provided, as a novel compound, a sulfonylsemicarbazide derivative having the general formula (I''):

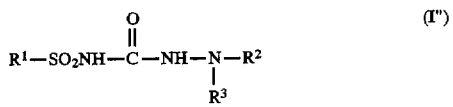 (I'')

wherein $R^1$ represents a linear or branched, lower alkyl group having 3 to 4 carbon atoms, or a phenyl group which may optionally be substituted by one or more halogen atoms, lower alkyl groups, hydroxyl groups, alkoxyl groups, carboxyl groups, alkoxycarbonyl groups, nitro groups, amino groups or benzyloxy groups, or $R^1$ represents a pyridyl group, or a thiophenyl group which may optionally be substituted by one or more carboxyl groups or alkoxycarbonyl groups, and $R^2$ and $R^3$ each independently represents a hydrogen atom, a lower alkyl group, an alkoxalyl group, an alkoxyalkyl group, an alkoxycarbonyl group or an alkylthio-thiocarbonyl group represented by the formula —C(X)—X—$R^4$ where X means an oxygen atom or a sulfur atom and $R^4$ means a lower alkyl group, or $R^2$ and $R^3$ may form a heterocyclic ring having 4 to 5 carbon atoms, as taken with the nitrogen atom to which $R^2$ and $R^3$ are bonded, or $R^2$ and $R^3$ may form a group of the formula —N=CR$^5$(R$^6$) where $R^5$ and $R^6$ mean lower alkyl groups, respectively, as taken with the nitrogen atom to which $R^2$ and $R^3$ are bonded, but with the proviso that (i) when $R^1$ is an alkoxycarbonyl-substituted phenyl group, $R^2$ and $R^3$ are both lower alkyl groups, (ii) when $R^1$ is phenyl group, p-methylphenyl group, p-chlorophenyl group, p-bromophenyl group, p-nitrophenyl group, p-aminophenyl group or p-methoxyphenyl group, $R^2$ and $R^3$ are not methyl groups or ethyl groups, respectively, at the same time, (iii) when $R^1$ is p-methylphenyl group or p-chlorophenyl group, $R^2$ and $R^3$ do not form a morpholino group, and (iv) when $R^1$ is phenyl group or p-methylphenyl group, $R^2$ and $R^3$ do not form a piperidino group; or a salt of said derivative.

Specific examples of the novel sulfonylsemicarbazide derivative represented by the general formula (I'') according to the fifth aspect of the present invention are shown along with their melting points in Table 3 and Table 4 given below. The Compound Nos. in Table 3 and Table 4 are the same as those shown in Table 1 and Table 2.

TABLE 3

Formula (I'')

$$R^1-SO_2-NH-\underset{\underset{R^3}{|}}{\overset{\overset{O}{\|}}{C}}-NH-N-R^2$$

| Comp'd No. | $R^1$ | $R^2$ | $R^3$ | m.p. (°C.) |
|---|---|---|---|---|
| 1 | 4-H₃C-C₆H₄- | CH₃ | H | 131~132.2 |
| 2 | C₆H₅- | CH₃ | H | 121~122 |
| 6 | 2-CH₃-C₆H₄- | CH₃ | CH₃ | 146~147 |
| 7 | 4-F-C₆H₄- | CH₃ | CH₃ | 143.5~144.5 |
| 10 | 4-HO-C₆H₄- | CH₃ | CH₃ | 175.5~176.5 |
| 12 | 4-H₃COOC-C₆H₄- | CH₃ | CH₃ | 171.5~172 |
| 15 | C₆H₅- | C₂H₄OC₂H₅ | C₂H₄OC₂H₅ | 74~76 |
| 16 | 4-H₃C-C₆H₄- | C₂H₄OC₂H₅ | C₂H₄OC₂H₅ | 91~92 |
| 17 | 4-Cl-C₆H₄- | C₂H₄OC₂H₅ | C₂H₄OC₂H₅ | 84.5~85.5 |
| 18 | C₆H₅- | H | COOCH₃ | 176.5~177.5 |
| 19 | C₆H₅- | H | COOC₂H₅ | 136~137.5 |
| 20 | 4-H₃C-C₆H₄- | H | COOC₂H₅ | 174~176 |
| 21 | C₆H₅- | H | CSSC₂H₅ | 140.5~141.5 |

TABLE 3-continued

Formula (I''')

$$R^1-SO_2-NH-C(=O)-NH-N(R^3)-R^2$$

| Comp'd No. | R¹ | R² | R³ | m.p. (°C.) |
|---|---|---|---|---|
| 22 | 4-methylphenyl (H₃C–C₆H₄–) | H | CSSCH₃ | 156–156.5 |
| 23 | phenyl | CH₃ | COCOOCH₃ | 165.5–166.5 |
| 24 | 4-(benzyloxy)phenyl (PhCH₂O–C₆H₄–) | CH₃ | CH₃ | 184–187 |
| 25 | H₃C–CH₂–CH₂– | CH₃ | CH₃ | 152.5–153 |
| 26 | (CH₃)₂CH– | CH₃ | CH₃ | 145–145.5 |
| 27 | 2-pyridyl | CH₃ | CH₃ | 172.5–174 |
| 28 | 3-pyridyl | CH₃ | CH₃ | 160–160.5 |
| 29 | 2-thienyl | CH₃ | CH₃ | 147.5–148.5 |
| 30 | 5-HOOC-2-thienyl | CH₃ | CH₃ | 206 (分解) |
| 31 | 5-H₃COOC-2-thienyl | CH₃ | CH₃ | 162–163 |

TABLE 4

Formula (I''')

$$R^1-SO_2-NH-C(=O)-NH-A$$

| Comp'd No. | R¹ | A | m.p. (°C.) |
|---|---|---|---|
| 33 | phenyl | –N(morpholino)O | 186–188 |
| 37 | 4-methylphenyl (H₃C–C₆H₄–) | 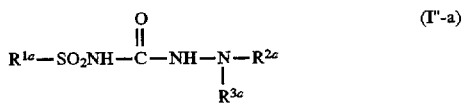 | 146 |

Preferred examples of the novel compound of the general formula (I''') according to the fifth aspect of the present invention include novel sulfonylsemicarbazide derivatives listed below under (1) to (9).

(1) Sulfonylsemicarbazide derivatives represented by the following general formula (I'''-a):

$$R^{1a}-SO_2NH-\underset{\underset{\displaystyle R^{3a}}{|}}{C(=O)-NH-N}-R^{2a} \qquad (I'''\text{-a})$$

wherein $R^{1a}$ is a 2-tolyl group, a fluorophenyl group, a hydroxyphenyl group, a benzyloxyphenyl group or an alkoxycarbonylphenyl group, and $R^{2a}$ and $R^{3a}$ are lower alkyl groups, respectively, (for example, Compounds No. 6, No. 7, No. 10, No. 12 and No. 24 in Table 3).

(2) Sulfonylsemicarbazide derivatives represented by the following general formula (I"-b):

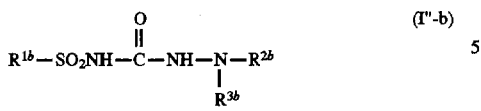

wherein $R^{1b}$ is a phenyl group which may be substituted by one or more lower alkyl groups, and one of $R^{2b}$ and $R^{3b}$ is a hydrogen atom but the other one of $R^{2b}$ and $R^{3b}$ is a lower alkyl group, preferably methyl group, (for example, Compounds No. 1 and No. 2 in Table 3).

(3) Sulfonylsemicarbazide derivatives represented by the following general formula (I"-c):

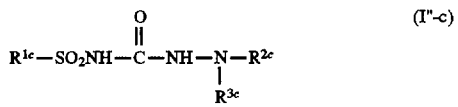

wherein $R^{1c}$ is a phenyl group which may be substituted by one or more lower alkyl groups or halogen atoms, and $R^{2c}$ and $R^{3c}$ are lower alkoxyalkyl groups, respectively, (e.g., Compounds No. 15, No. 16 and No. 17 in Table 3).

(4) Sulfonylsemicarbazide derivatives represeted by the following general formula (I"-d):

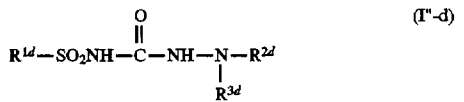

wherein $R^{1d}$ is a phenyl group which may be substituted by one or more lower alkyl groups, and one of $R^{2d}$ and $R^{3d}$ is an alkoxalyl group or an alkoxycarbonyl or alkylthiothiocarbonyl group represented by the formula —C(X)—X—$R^4$ where X means an oxygen atom or a sulfur atom and $R^4$ means a lower alkyl group, but the other one of $R^{2d}$ and $R^{3d}$ is a hydrogen atom or a lower alkyl group (for example, Compounds No. 18, No. 19, No. 20, No. 21, No. 22 and No. 23 in Table 3).

(5) Sulfonylsemicarbazide derivatives represeted by the following general formula (I"-e):

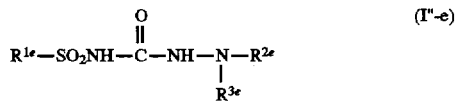

wherein $R^{1e}$ is phenyl group, and $R^{2e}$ and $R^{3e}$ form a morpholino group as taken with the nitrogen atom to which $R^{2e}$ and $R^{3e}$ are bonded (for example, Compound No. 33 in Table 4).

(6) Sulfonylsemicarbazide derivatives represented by the following general formula (I"-f):

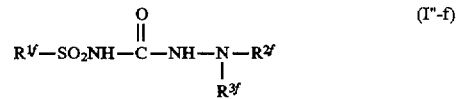

wherein $R^{1f}$ is a phenyl group which may be substituted by one or more lower alkyl groups, and $R^{2f}$ and $R^{3f}$ form a group of the formula —N=$CR^5(R^6)$ where $R^5$ and $R^6$ each independently mean a lower alkyl group, as taken with the nitrogen atom to which $R^{2f}$ and $R^{3f}$ are bonded (for example, Compound No. 37 in Table 4).

(7) Sulfonylsemicarbazide derivatives represented by the following general formula (I"-g):

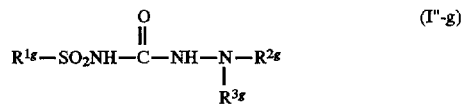

wherein $R^{1g}$ is a linear or branched, lower alkyl group having 3 to 4 carbon atoms, and $R^2g$ and $R^3g$ are alkyl groups having 1 to 2 carbon atoms, respectively (for example, Compounds No. 25 and No. 26 in Table 3).

(8) Sulfonylsemicarbazide derivatives represented by the following general formula (I"-h):

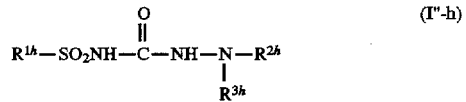

wherein $R^{1h}$ is a pyridine-2-yl group or a pyridine-3-yl group, and $R^{2h}$ and $R^{3h}$ are alkyl groups having 1 to 2 carbon atoms, respectively (for example, Compounds No. 27 and No. 28 in Table 3).

(9) Sulfonylsemicarbazide derivatives represented by the following general formula (I"-i):

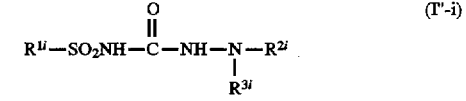

wherein $R^{1i}$ is a thiophen-2-yl or thiophen-3-yl group which may be substituted by one or more carboxyl groups or lower alkoxycarbonyl groups, and $R^{2i}$ and $R^{3i}$ are alkyl groups having 1 to 2 carbon atoms, respectively, (for example, Compounds No. 29, No. 30 and No. 31 in Table 3).

The present invention will next be illustrated by exemplifying the production of some examples of the compound of the general formula (I") according to the fifth aspect of the present invention in the following Synthesis Examples. It is however borne in mind that the present invention shall not be limited by these Examples.

Synthesis Example 1

Synthesis of 1-ethoxycarbonyl-4-(4-methylphenyl-sulfonyl)semicarbazide (Compound No. 20 in Table 3)

Ethyl carbamate (1.1 g) and 4-tolylsulfonyl isocyanate (2.2 g) were dissolved in 30 ml of anhydrous dichloromethane. Upon stirring the resultant solution under ice cooling, crystals were formed immediately. After the stirring was continued for 1 hour, the crystals were collected from the reaction mixture by filtration and were then washed with dichloromethane. The crystals were then dried to afford 2.65 g of the target compound. Melting Point: 174°–176° C. Yield: 88%.

Synthesis Example 2

Synthesis of 1,1-di(2-ethoxyethyl)-4-(4-chlorophenylsulfonyl)semicarbazide (Compound No. 17 in Table 3)

Mixed were 2.6 g of 4-chlorophenylsulfonyl-ethyl carbamate and 1.8 g of 1,1-bis(ethoxyethyl)hydrazine. The resulting mixture was subjected to reaction at 110° C. for 15 minutes, and the reaction product was obtained in the form of a reddish brown oil. The reaction product was subjected to silica gel column chromatography, followed by development with hexaneethyl acetate (1:1) as a developing solvent so that fractions corresponding to the target compound were collected. After those fractions were concentrated, the resulting the concentrate was recrystallized from hexane, to obtain 1.8 g of white crystals. Melting point: 84.5°–85.5° C. Yield: 47%

Synthesis Example 3

Synthesis of 1,1-dimethyl-4-(4-fluorophenylsulfonyl) semicarbazide (Compound No. 7 in Table 3)

4-Fluorophenylsulfonyl-ethyl carbamate (3.1 g) was dissolved in 30 ml of xylene. After addition of 1.8 g of 1,1-dimethylhydrazine to the resultant solution, the resulting mixture was subjected to the reaction at 115° C. for 20 minutes. When the reaction solution obtained was allowed to cool down, an oily substance separated and solidified. The solid was collected by filtration and washed with toluene to afford 4.25 g of the target compound desired. Melting point: 143.5–144.5° C. Yield: 81%.

Besides, by following the procedures of Synthesis Example 1 to Synthesis Example 3, the novel compounds as shown in Table 3 and Table 4 were further synthesized.

Now, the following Test Examples 1–6 were conducted to demonstrate that the compounds of the general formula (I) have the effects for preserving the freshness of the flower petals of cut flowers.

Test Example 1

This Example shows that the compounds of the general formula (I) according to the present invention are effective for preserving or maintaining the freshness of cut flowers of carnation.

Plants of carnation with flowers (variety: Francisco) which were grown by a flower grower in Hatano city, Kanagawa-ken, Japan, were cut at their lower stem portions so that the resulting cut flowers of carnation had a stem length of 10 cm. In cylindrical bottles (3 cm in diameter, 12 cm in height) which were filled with 50 ml portions of aqueous solutions containing the test compounds at a concentration of 10 ppm, respectively one length of the cut flowers was placed in each bottle so that the lower stem end of the cut flower was soaked in the aqueous solution. The cut flowers were then stored in an air-conditioned room controlled at 25° C., while the conditions of the petals of the cut flowers were observed. Each test group of the cut flowers was tested with four replications. For the sake of comparison, a control test was also conducted without addition of any test compound. The results are tabulated in Table 5.

TABLE 5

| Test Compound No. | Days after the start of soaking treatment | | | | |
|---|---|---|---|---|---|
| | 0 | 2 | 4 | 6 | 8 |
| No chemical added | − | ± | ± | ++ | ++ |
| 1 | − | − | ± | ± | + |
| 3 | − | − | − | − | ± |
| 4 | − | − | − | ± | + |
| 5 | − | − | − | ± | ± |
| 6 | − | − | − | ± | + |
| 8 | − | − | − | − | ± |

− No petal wilted    ± Petal wilting started
+ Petal wilting worsened    ++ Petals completely wilted As is evident from Table 5, all the tested compounds showed the effects for preserving the freshness of the petals of cut carnation flowers.

Test Example 2

This Example also demonstrates that the compounds according to the present invention have the effects for preserving the freshness of the flower petals of cut carnation flowers.

The tests were conducted in the same manner as in Test Example 1. The results are tabulated in Table 6.

TABLE 6

| Test Compound No. | Days after the start of soaking treatment | | | | |
|---|---|---|---|---|---|
| | 0 | 2 | 4 | 6 | 8 |
| No chemical added | − | − | ± | + | ++ |
| 9 | − | − | − | − | ± |
| 16 | − | − | − | ± | + |
| 19 | − | − | − | ± | + |
| 20 | − | − | − | − | + |
| 21 | − | − | − | − | ++ |
| 22 | − | − | − | ± | ++ |
| 32 | − | − | − | + | + |
| 33 | − | − | − | ± | ++ |
| 34 | − | − | − | ± | ++ |
| 35 | − | − | − | ± | + |
| 36 | − | − | − | ± | ++ |

− No petal wilted    ± Petal wilting started
+ Petal wilting worsened    ++ Petals completely wilted As is evident from Table 6, all the tested compounds showed the effects for preserving the freshness of cut carnation flowers.

Test Example 3

Tests were conducted on cut carnation flowers in the same manner as in Test Example 1. The results are summarized in Table 7.

TABLE 7

| Test Compound No. | Days after the start of soaking treatment | | | | | |
|---|---|---|---|---|---|---|
| | 0 | 2 | 4 | 6 | 8 | 10 |
| No chemical added | − | − | − | ± | ++ | ++ |
| 7 | − | − | − | − | + | ++ |
| 11 | − | − | − | − | ± | + |
| 12 | − | − | − | − | + | ++ |
| 15 | − | − | − | − | + | + |
| 17 | − | − | − | − | + | + |
| 18 | − | − | − | − | + | ++ |
| 27 | − | − | − | − | − | − |

− No petal wilted    ± Petal wilting started
+ Petal wilting worsened    ++ Petals completely wilted As is evident from Table 7, all the tested compounds showed the effects for preserving the freshness of cut flowers.

Test Example 4

The tests were conducted on cut carnation flowers in the same manner as in Test Example 1. The results are shown in Table 8.

TABLE 8

| Test Compound No. | Days after the start of soaking treatment | | | | | |
|---|---|---|---|---|---|---|
| | 0 | 2 | 4 | 6 | 8 | 10 |
| No chemical added | − | − | − | ++ | ++ | ++ |
| 10 | − | − | − | ± | ++ | ++ |
| 13 | − | − | − | − | ± | ++ |
| 14 | − | − | − | − | ± | ++ |
| 24 | − | − | − | − | ± | ++ |
| 25 | − | − | − | − | + | ++ |
| 26 | − | − | − | ± | + | ++ |
| 27 | − | − | − | − | − | ++ |
| 28 | − | − | − | ± | ++ | ++ |
| 29 | − | − | − | − | − | − |
| 30 | − | − | − | ± | ++ | ++ |
| 31 | − | − | − | − | − | + |

− No petal wilted   + Petal wilting started
+ Petal wilting worsened   ++ Petals completely wilted As is evident from Table 8, all the tested compounds showed the effects for preserving the freshness of cut carnation flowers.

Test Example 5

The tests were conducted on cut carnation flowers in the same manner as in Test Example 1. The results are shown in Table 9.

TABLE 9

| Test Compound No. | Days after the start of soaking treatment | | | | | |
|---|---|---|---|---|---|---|
| | 0 | 2 | 4 | 6 | 8 | 10 |
| No chemical added | − | − | + | ++ | ++ | ++ |
| 37 | − | − | − | − | − | ± |

− No petal wilted   ± Petal wilting started
+ Petal wilting worsened   ++ Petals completely wilted As is evident from Table 9, Compound No. 37 showed the effects for preserving the freshness of cut carnation flowers.

Test Example 6

Plants of carnation with flowers which were similar to those employed in Test Example 1 were cut at their stems to a stem length of 50 cm. Three lengths of the resulting cut carnation flowers were placed in each of flasks filled with an aqueous solution containing the test compound at varying concentrations indicated in Table 10. The cut flowers were stored in an air-conditioned room controlled at 25° C., and the cut flowers were allowed for 16 hours to absorb the test compound solution through the cut stem ends of them. The cut flowers were then transferred to a flask filled with deionized water, and thereafter the conditions of the petals of the cut flowers were observed. Each test group of the cut flowers was tested with two replications. For the sake of comparison, a comparative test was conducted with using STS as the test compound. The results are presented in Table 10.

TABLE 10

| Test Compound No. | Concentration of test compound | Days after the transfer in deionized water | | | |
|---|---|---|---|---|---|
| | | 0 | 2 | 4 | 6 | 8 |
| No chemical added | | − | ± | + | ++ | ++ |
| STS (comparative) | 0.2 mM | − | ± | ± | ± | + |
| 3 | 0.04 | − | − | ± | ± | + |
| | 0.2 | − | − | ± | ± | + |
| | 1.0 | − | − | ± | ± | + |
| 8 | 0.04 | − | ± | ± | + | + |
| | 0.2 | − | − | ± | ± | + |
| | 1.0 | − | ± | ± | + | + |

− No petal wilted   ± Petal wilting started
+ Petal wilting worsened   ++ Petals completely wilted As is evident from Table 10, the pulse treatment done with the above test compounds can show the effects for preserving the freshness of the flowers to a same degree as or a greater degree than STS which was employed as the comparative agent.

INDUSTRIAL UTILIZABILITY OF INVENTION

According to the present invention, there is provided an agent for preserving the freshness of the flower petals of cut flowers for a prolonged period with retaining favourable conditions of the flower petals, which is useful since said agent can extend such life period of flowers during which the worth of the flower petals of the cut flowers or flower petals of a plant of the florist crop being cultivated can be enjoyed.

We claim:

1. A sulfonylsemicarbazide derivative of the general formula (I''), which is a compound having the general formula (I''-h):

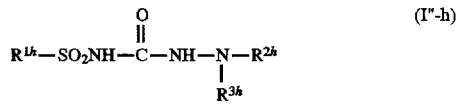

wherein $R^{1h}$ is a pyridine-2-yl group or a pyridine-3-yl group, and $R^{2h}$ and $R^{3h}$ are alkyl groups having 1 to 2 carbon atoms, respectively, or a salt thereof.

2. A sulfonylsemicarbazide derivative of the general formula (I''), which is a compound having the general formula (I''-i):

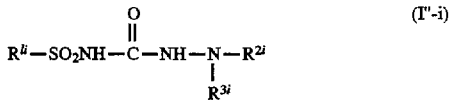

wherein $R^{1i}$ is a thiophen-2-yl or thiophen-3-yl group which may be substituted by one or more carboxyl groups or lower alkoxycarbonyl groups, and $R^{2i}$ and $R^{3i}$ are alkyl groups having 1 to 2 carbon atoms, respectively, or a salt thereof.

3. The derivative according to claim 1, which is 1,1-dimethyl-4-(pyridine-2-ylsulfonyl)semicarbazide or 1,1-dimethyl-4-(pyridine-3-ylsulfonyl)semicarbazide.

4. The derivative according to claim 2, which is 1,1-dimethyl-4(thiophen-2-ylsulfonyl)semicarbazide, 1,1-dimethyl-4-(4-carboxy-thiophen-3-ylsulfonyl)semicarbazide or 1,1-dimethyl-4-(4-methoxycarbonyl-thiophen-3-ylsulfonyl)-semicarbazide.

5. A composition for preserving the freshness of flower petals of cut flowers, which comprises as an effective ingredient at least one sulfonylsemicarbazide derivative having the general formula (I-h):

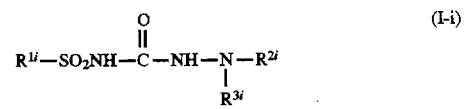

wherein $R^{1h}$ is a pyridine-2-yl group or a pyridine-3-yl group, and $R^{2h}$ and $R^{3h}$ are alkyl groups having 1 to 2 carbon atoms, respectively, or salts of said derivatives.

6. The composition for preserving the freshness of flower petals of cut flowers, which comprises as an effective ingredient at least one sulfonylsemicarbazide derivative having the general formula (I-i):

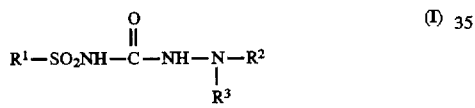

wherein $R^{1i}$ is a thiophen-2-yl or thiophen-3-yl group which may be substituted by one or more carboxyl groups or lower alkoxycarbonyl groups, and $R^{2i}$ and $R^{3i}$ are alkyl groups having 1 to 2 carbon atoms, respectively, or salts of said derivatives.

7. A method for preserving the freshness of flowers of a plant of the florist crop, which comprises treating the cut stem portion or leaves of the cut flowers as obtained by cutting off the root part of the florist plant, or treating roots or leaves of the florist plant under cultivation in a field or a pot, with a sulfonylsemicarbazide derivative having the general formula (I):

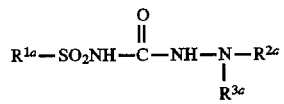

wherein $R^1$ represents a linear or branched, lower alkyl group having 3 to 4 carbon atoms, or a phenyl group which may optionally be substituted by one or more halogen atoms, lower alkyl groups, hydroxyl groups, alkoxyl groups, carboxyl groups, alkoxycarbonyl groups, nitro groups, amino groups or benzyloxy groups, or $R^1$ represents a pyridyl group, or a thiophenyl group which may optionally be substituted by one or more carboxyl groups or alkoxycarbonyl groups, and $R^2$ and $R^3$ each independently represents a hydrogen atom, a lower alkyl group, an alkoxalyl group, an alkoxyalkyl group, an alkoxycarbonyl group or an alkylthio-thiocarbonyl group represented by the formula —C(X)—X—$R^4$ where X means an oxygen atom or a sulfur atom and $R^4$ means a lower alkyl group, or $R^2$ and $R^3$ may form a heterocyclic ring having 4 to 5 carbon atoms, as taken with the nitrogen atom to which $R^2$ and $R^3$ are bonded, or $R^2$ and $R^3$ may form a group of the formula —N=CR$^5$(R$^6$) where $R^5$ and $R^6$ mean lower alkyl groups, respectively, as taken with the nitrogen atom to which $R^2$ and $R^3$ are bonded, or salts of said derivatives, or with an aqueous solution of said derivative(s) or said salt(s), and thereby allowing the cut flowers or the florist plant under the cultivation to absorb the compound of the general formula (I) in an amount effective to maintain the freshness of the flower.

8. The method according to claim 7, wherein the sulfonylsemicarbazide derivative of the formula (I) employed is the derivative of the formula (I-a):

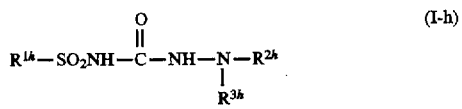

wherein $R^{1a}$ is a linear or branched, lower alkyl group having 3 to 4 carbon atoms, a phenyl group, a 2-tolyl group, a fluorophenyl group, a hydroxyphenyl group, a benzyloxyphenyl group, an alkoxycarbonylphenyl group or a pyridyl group, or $R^{1a}$ is a thiophenyl group which may optionally be substituted by one or more carboxyl groups or alkoxycarbonyl groups, and $R^{2a}$ and $R^{3a}$ are lower alkyl groups, respectively; the derivative of the formula (I-b):

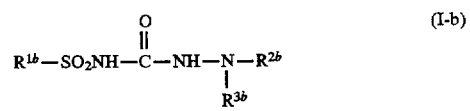

wherein $R^{1b}$ is a phenyl group which may be substituted by one or more lower alkyl groups, and one of $R^{2b}$ and $R^{3b}$ is a hydrogen atom but the other one of $R^{2b}$ and $R^{3b}$ is a lower alkyl group; the derivative of the formula (I-c):

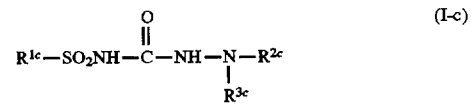

wherein $R^{1c}$ is a phenyl group which may be substituted by one or more lower alkyl groups or halogen atoms, and $R^{2c}$ and $R^{3c}$ are lower alkoxyalkyl groups, respectively; the derivative having the formula (I-d):

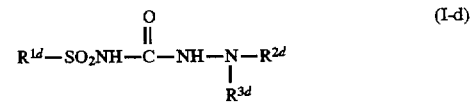

wherein $R^{1d}$ is a phenyl group which may be substituted by one or more lower alkyl groups, and one of $R^{2d}$ and $R^{3d}$ is an alkoxyalkyl group, an alkoxycarbonyl group or an alkylthio-thiocarbonyl group represented by the formula —C(X)—X—$R^4$ where X means an oxygen atom or a sulfur atom and $R^4$ means a lower alkyl group, but the other one of $R^{2d}$ and $R^{3d}$ is a hydrogen atom or a lower alkyl group; the derivative of the formula (I-e):

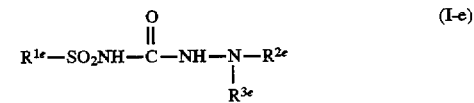

wherein $R^{1e}$ is a phenyl group which may be substituted by one or more lower alkyl groups or halogen atoms, and $R^{2e}$ and $R^{3e}$ form a morpholino group or a piperidino group, as taken with the nitrogen atom to which $R^{2e}$ and $R^{3e}$ are bonded; the derivative having the formula (I-f):

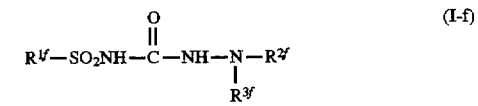

wherein $R^{1f}$ is a phenyl group which may be substituted by one or more lower alkyl groups, and $R^{2f}$ and $R^{3f}$ form a group of the formula —N=CR$^5$(R$^6$) where $R^5$ and $R^6$ each independently mean a lower alkyl group, as taken with the nitrogen atom to which $R^{2f}$ and $R^{3f}$ are bonded; the derivative of the formula (I-g):

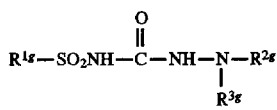

(I-g)

wherein $R^{1g}$ is a linear or branched, lower alkyl group having 3 to 4 carbon atoms, and $R^{2g}$ and $R^{3g}$ are alkyl groups having 1 to 2 carbon atoms, respectively; the derivative of the general formula (I-h):

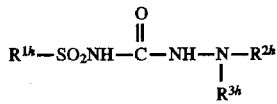

(I-h)

wherein $R^{1h}$ is a pyridine-2-yl group or a pyridine-3-yl group, and $R^{2h}$ and $R^3$ are alkyl groups having 1 to 2 carbon atoms, respectively; or the derivative of the formula (I-i):

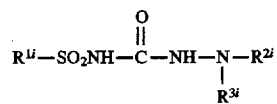

(I-i)

wherein $R^{1i}$ is a thiophen-2-yl or thiophen-3-yl group which may be substituted by one or more carboxyl groups or lower alkoxycarbonyl groups, and $R^{2i}$ and $R^{3i}$ are alkyl groups having 1 to 2 carbon atoms, respectively.

9. The method according to claim 7, wherein the derivative of the formula (I) employed is selected from the group consisting of 1,1-dimethyl-4-(phenylsulfonyl) semicarbazide, 1,1-dimethyl-4-(p-methylphenyl-sulfonyl) semicarbazide and 1,1-dimethyl-4-(p-chlorophenylsulfonyl)-semicarbazide.

10. The method according to claim 7, wherein the derivative of the formula (I) employed is selected from the group consisting of 1,1-dimethyl-4-(pyridine-2-ylsulfonyl) semicarbazide, 1,1-dimethyl-4-(pyridine-3-ylsulfonyl) semicarbazide, 1,1-dimethyl-4-(thiophen-2-ylsulfonyl)-semicarbazide, 1,1-dimethyl-4-(4-carboxy-thiophen-3-ylsulfonyl)-semicarbazide and 1,1-dimethyl-4-(4-methoxycarbonyl-thiophen-3-ylsulfonyl)semicarbazide.

11. The method according to claim 8, wherein $R^{2b}$ or $R^{3b}$ in the derivative of formula (I-b) is a methyl group.

* * * * *

UNITED STATES PATENT AND TRADEMARK OFFICE
CERTIFICATE OF CORRECTION

PATENT NO. : 5,723,407
DATED : March 3, 1998
INVENTOR(S) : Naoki MIDOU et al.

It is certified that error appears in the above-identified patent and that said Letters Patent is hereby corrected as shown below:

On the title page, item [54] and column 1, line 4, delete "FLOWER OF"

<u>IN THE ABSTRACT</u> (wherein each formula represents one line of text)

Category [57], line 4, change "a flower" to --flowers--

Line 6, after "enjoyed." insert --These derivatives have the formula--

Line 11, change "represent" to --represents--

Line 14, change "other" to --others--

UNITED STATES PATENT AND TRADEMARK OFFICE
CERTIFICATE OF CORRECTION

PATENT NO. : 5,723,407
DATED : March 3, 1998
INVENTOR(S) : Naoki MIDOU et al.

It is certified that error appears in the above-identified patent and that said Letters Patent is hereby corrected as shown below:

Column 2

Line 2, change "dirts" to --dirt--

Line 19, change "primarilly" to --primarily--

Line 38, change "their inhibiting" to --inhibiting--

Column 3

Line 38, change "flower" to --flowers--

Column 4

Line 48, before "Synthesis Examples" insert --in--

UNITED STATES PATENT AND TRADEMARK OFFICE
CERTIFICATE OF CORRECTION

PATENT NO. : 5,723,407
DATED : March 3, 1998
INVENTOR(S) : Naoki MIDOU et al.

It is certified that error appears in the above-identified patent and that said Letters Patent is hereby corrected as shown below:

Column 9

Table 2, line 25, change "Compounr" to --Compound--

Line 53, change "The compounds of Compound No. 3" to --Compound No. 3--

Line 54, delete "the"

Line 55, delete "compounds of"

Line 57, delete "The compound of"

Line 60, delete "the compounds of"

Column 12

Line 62, before "aqueous" insert --an--

Line 64, before "powder" insert --a-- and delete "with"

UNITED STATES PATENT AND TRADEMARK OFFICE
CERTIFICATE OF CORRECTION

PATENT NO. : 5,723,407
DATED : March 3, 1998
INVENTOR(S): Naoki MIDOU et al.

It is certified that error appears in the above-identified patent and that said Letters Patent is hereby corrected as shown below:

Column 13

Line 46, delete "its"

Line 59, before "optimal" insert --the--

Column 14

Line 8, change "flower" to --flowers--

Line 44, before "cut flower" insert --a--

Line 59, change "should be" to --is--

Column 15

Line 26, before "reaction" insert --the--

Line 48, change "In the" to --In these--

UNITED STATES PATENT AND TRADEMARK OFFICE
CERTIFICATE OF CORRECTION

PATENT NO. : 5,723,407
DATED : March 3, 1998
INVENTOR(S) : Naoki MIDOU et al.

It is certified that error appears in the above-identified patent and that said Letters Patent is hereby corrected as shown below:

Column 16

Line 2, change "xylen" to --xylene--

Line 44, before "phenyl" insert --a--

Line 48, before "p-methylphenyl" insert --a--

Line 50, before "phenyl" insert --a--

Column 21

Line 26, change "represeted" to --represented--

Line 43, change "represeted" to --represented--

Line 50, before "phenyl" insert --a--

Column 23

Line 3, delete "the"

Column 25

Line 65, delete "with"

UNITED STATES PATENT AND TRADEMARK OFFICE
CERTIFICATE OF CORRECTION

PATENT NO. : 5,723,407
DATED : March 3, 1998
INVENTOR(S) : Naoki MIDOU et al.

It is certified that error appears in the above-identified patent and that said Letters Patent is hereby corrected as shown below:

Column 26

Line 19, change "can show" to --shows--

Line 20, change "a same" to --the same--

Line 27, change "with" to --while--

Line 29, change "such" to --the--

Signed and Sealed this

Nineteenth Day of January, 1999

Attest:

Attesting Officer

*Acting Commissioner of Patents and Trademarks*